(12) United States Patent
Metzger

(10) Patent No.: US 7,153,326 B1
(45) Date of Patent: Dec. 26, 2006

(54) METHOD AND APPARATUS FOR USE OF AN OFFSET STEM CONNECTION

(75) Inventor: Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 102 days.

(21) Appl. No.: 10/465,056

(22) Filed: Jun. 19, 2003

(51) Int. Cl.
*A61F 2/38* (2006.01)

(52) U.S. Cl. .................. 623/20.15; 623/20.14

(58) Field of Classification Search .................. 439/66, 439/74, 86, 91, 591; 623/20.14, 20.15, 20.21, 623/20.28, 20.29–20.33, 20.11, 21.11, 22.42, 623/23.15
See application file for complete search history.

(56) References Cited

U.S. PATENT DOCUMENTS

| | | | |
|---|---|---|---|
| 4,676,797 A | 6/1987 | Anapliotis et al. | |
| 4,950,297 A | 8/1990 | Elloy et al. | |
| 4,995,883 A | 2/1991 | Demane et al. | |
| 5,286,253 A | 2/1994 | Fucci | |
| 5,609,642 A | 3/1997 | Johnson et al. | |
| 5,643,303 A | 7/1997 | Donahue | |
| 5,776,200 A | 7/1998 | Johnson et al. | |
| 5,782,920 A | 7/1998 | Colleran | |
| 5,782,921 A | 7/1998 | Colleran et al. | |
| 6,063,091 A | 5/2000 | Lombardo et al. | |
| 6,146,424 A | 11/2000 | Gray, Jr. et al. | |
| 6,149,687 A | 11/2000 | Gray, Jr. et al. | |
| 6,162,255 A | 12/2000 | Oyola | |
| 6,171,342 B1 | 1/2001 | O'Neil et al. | |
| 6,214,052 B1 | 4/2001 | Burkinshaw | |
| 6,217,619 B1 | 4/2001 | Keller | |
| 6,228,091 B1 | 5/2001 | Lombardo et al. | |
| 6,306,172 B1 | 10/2001 | O'Neil et al. | |
| 6,505,387 B1 | 1/2003 | Yatskov et al. | |
| 2003/0055508 A1* | 3/2003 | Metzger et al. | 623/20.15 |
| 2003/0180117 A1* | 9/2003 | Niku | 411/392 |
| 2003/0204263 A1* | 10/2003 | Justin et al. | 623/20.15 |

OTHER PUBLICATIONS

Biomet Offset Tibia; Biomet Orthopedics, Inc., Dec. 2001.

* cited by examiner

*Primary Examiner*—Alvin J. Stewart
(74) *Attorney, Agent, or Firm*—Harness, Dickey & Pierce, P.L.C.

(57) ABSTRACT

A modular tibial component for a knee joint prosthesis providing an offset. The modular tibial component includes a tray, a stem, an adapter and a flexible fastener. The tray includes a tapered extension having a generally frusto-conical shape. The stem includes a finned surface and an extension having a generally frusto-conical shape. The adapter connects the tray and the stem while providing an offset therebetween. The adapter includes a first generally frusto-conical cavity receiving the tapered extension of the tray and a second generally frusto-conical cavity receiving the upwardly extension of the stem. The flexible fastener is inserted through an aperture in the tray and a cavity in the adapter and fastened to the stem.

23 Claims, 3 Drawing Sheets

METHOD AND APPARATUS FOR USE OF AN OFFSET STEM CONNECTION

FIELD OF THE INVENTION

The present invention relates generally to a joint prosthesis and more particularly to a knee joint prosthesis having a modular tibial component with an offset tibial stem.

BACKGROUND OF THE INVENTION

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of motion.

A typical tibial component is secured to the tibia with a stem that is implanted within the medullary canal. The stem connects to a tibial tray that provides a bearing surface for engagement with the femoral component. In this regard, in a normally shaped tibia, the medullary canal is typically offset from the center of the tibial articulating surfaces or the center of the tibial plateau. The tibial tray will be centered on a resected tibial plateau and includes an anterior edge and a posterior edge that are generally required to be of a differing shape. In order to provide a modular tibial component that is interchangeable between a right knee and a left knee, the tibial tray is typically provided with a central aperture for connection to an offset stem. The stems of prior tibial implants are required to be of differing lengths and diameters to accommodate the differing sizes of tibias while providing optimal strength and bone engagement. While these known knee joint prostheses may be effective in replacing the anatomical knee joint, they require that a multitude of stems be available for replacement surgery.

To a more limited extent, it is also known to provide a knee joint prosthesis with a fixed offset adapter for the tibia stem. The required variation of stem sizes and adapter sizes reduces the number components that must be available to perform the replacement surgery. These adapters typically have a fixed offset direction with respect to the stem and require multiple connections be made during the surgical procedure. While knee joint prosthesis with offset tibial stem adapters may provide certain identified advantages, they nevertheless can be the subject of certain improvement. What is needed is an apparatus for providing an offset for a modular tibial component that requires fewer stems, adapters and fasteners than the prior art, while allowing the offset in any direction relative the stem.

SUMMARY OF THE INVENTION

In accordance with the teachings of the present invention, a method and apparatus for an offset connection of a tibial tray and a stem for a knee joint prosthesis is disclosed.

In one form, the present invention provides a modular assembly for a knee joint prosthesis having an implant base, a stem, and an adapter body configured to establish a relative offset between the implant base and the stem, and a flexible fastener interconnecting the implant base and the stem.

In another form, the present invention provides a method of providing an offset between prosthetic components. The method includes positioning an offset adapter adjacent a first coupling portion, positioning the offset adapter relative a second coupling portion and fastening the implant base to the offset adapter with a flexible fastener.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiments of a method and apparatus for assembling a tibial component with an offset adapter for a knee joint prosthesis are merely exemplary in nature and is in no way intended to limit the invention, its application, or uses. Moreover, while the present invention is described in detail with reference to an offset tibial adapter, it will be appreciated by those skilled in the art that the present invention is not limited to an offset tibial adapter, but may also be used with any other prosthesis that requires an offset. It should also be appreciated that the adapters, while described herein with specific dimensions, could be any appropriate dimension, or provide any desired amount of offset.

Figure 1:
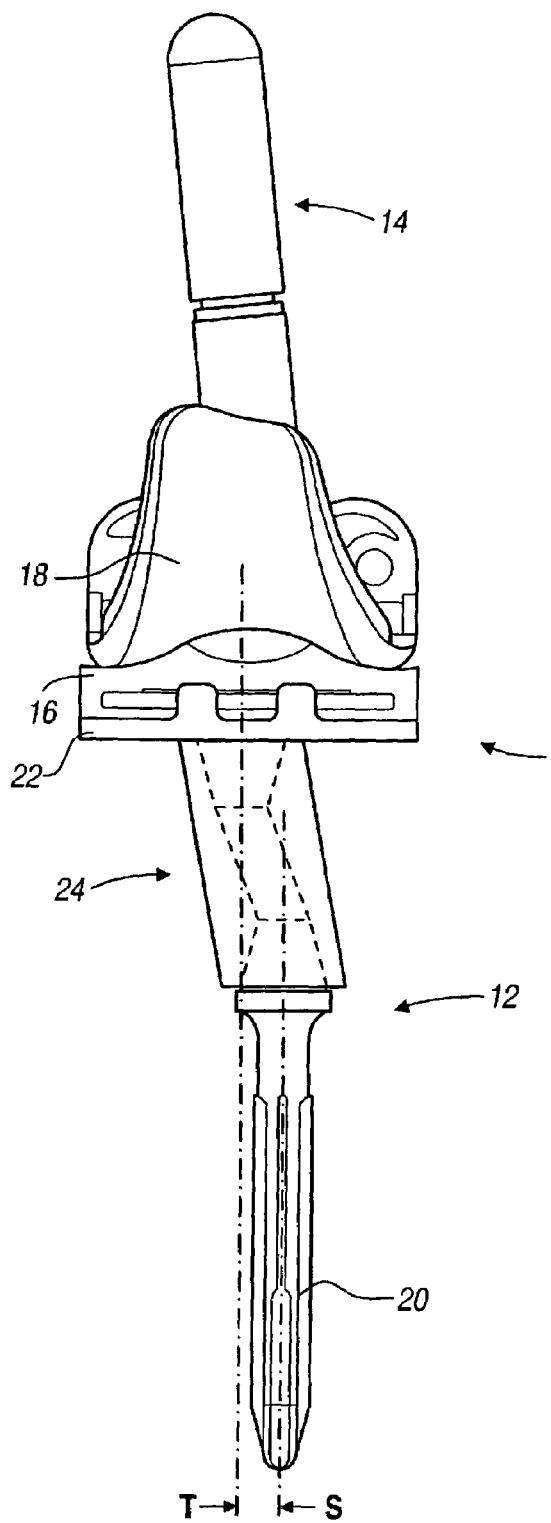
FIG. 1 is an anterior view of a knee joint prosthesis, the knee joint prosthesis is illustrated to include a first adapter for providing a first predetermined offset and a flexible fastener according to the teachings of the present invention.

With initial reference to FIG. 1, a knee joint prosthesis constructed in accordance with the teachings of the present invention is illustrated and generally identified at reference number 10. The knee joint prosthesis 10 is generally shown to include a first, or tibial, component 12 and a second, or femoral, component 14. The tibial component 12 supports a bearing 16 which engages an articulation surface 18 of the femoral component 14. Insofar as the present invention is concerned, it will be understood that the femoral component 14 and the bearing 16 shown in FIG. 1 are conventional in construction. In this regard, the knee joint prosthesis may be a cruciate retaining, posterior stabilized, fully constrained or hinged prosthesis, and may have a fixed or mobile bearing.

Figure 2:
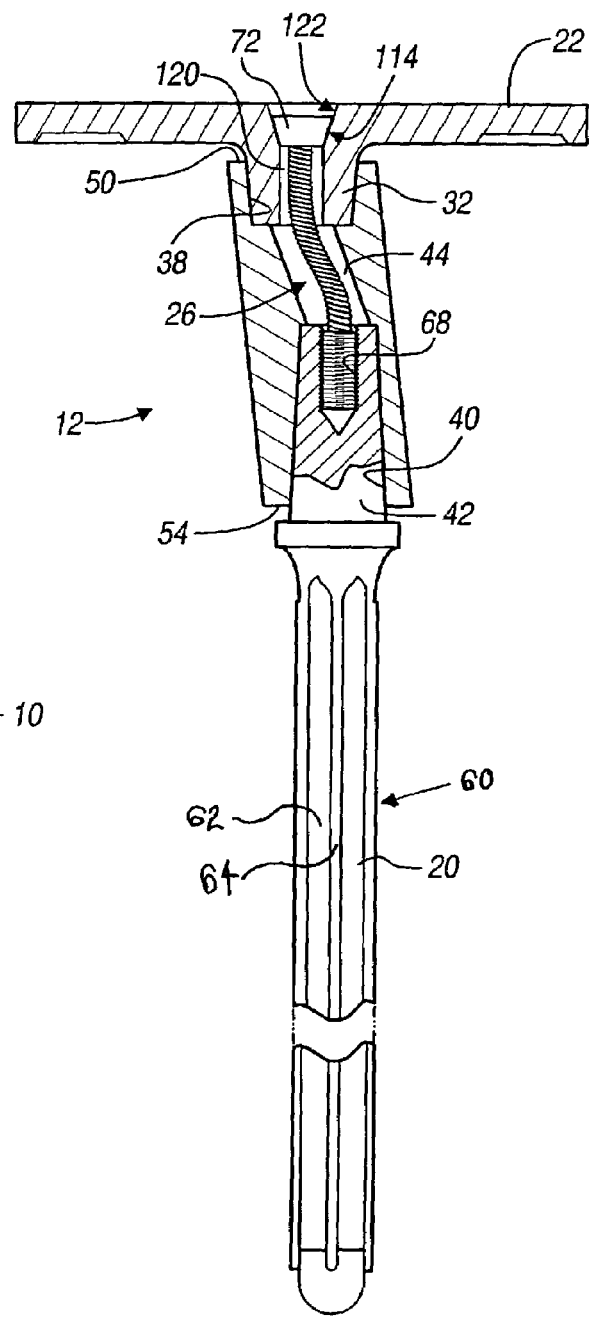
FIG. 2 is an anterior partial cross-sectional view of a modular tibial component of the knee joint prosthesis of FIG. 1.

FIG. 2 illustrates the tibial component 12 which will be understood to be modular or integral in construction and to generally include a second portion, or stem, 20, an implant base, or tray, 22, a first adapter 24 and a flexible fastener 26. In a manner which will be discussed more fully below, the first adapter 24 connects the tray 22 and the stem 20 so as to provide an offset therebetween in the general medial-lateral plane. Explaining further, when the stem 20 is attached to the tray 22 through the first adapter 24, a central axis S of the stem 20 is offset from a central axis T of a tapered extension 32 of the tray 22. In the embodiment illustrated, the first adapter 24 provides a first offset $O_1$ of approximately 5 mm. It will become apparent below that the offset can be in any direction relative to the central axis S.

Figure 4:
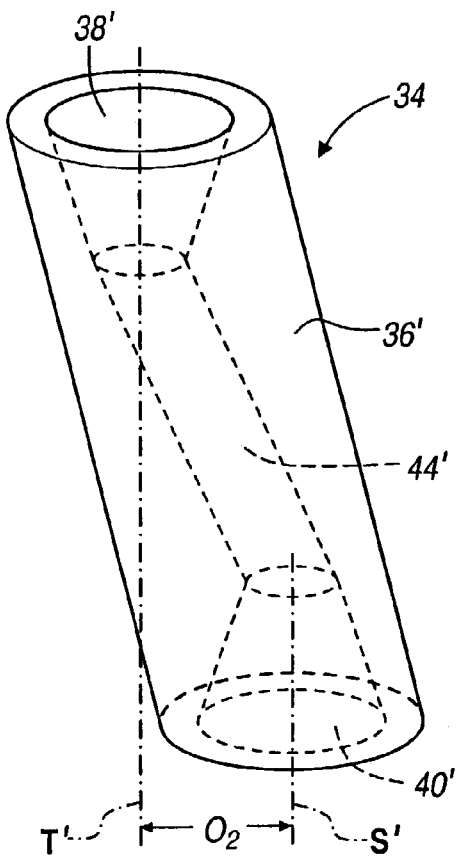
FIG. 4 is a perspective view of a second adapter assembly according to the teachings of the present invention.

With brief reference to FIG. 4, a second adapter 34 according to the teachings of the present invention, is illustrated. The second adapter 34 is configured to connect the tray 22 and stem 20 of FIG. 1. As will be discussed more fully below, the second adapter 34 provides a second offset $O_2$ which in the embodiment illustrated is approximately 2 mm. Explaining further, a tibial component assembled with second adapter 34 would include a central axis S' of the stem 20 which is offset 2 mm with the central axis T' of the tapered extension 32 of the tray 22. It will be appreciated by those skilled in the art that the particular amounts of offset provided by the various adapters of the present invention are not limited. Alternate offsets will be understood to fall within the scope of the present invention.

Figure 3:
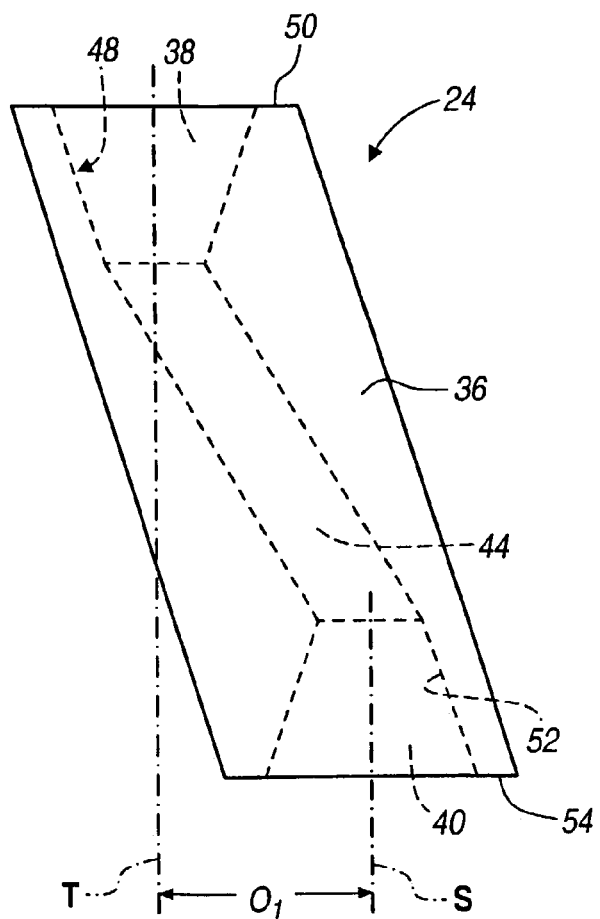
FIG. 3 an anterior view of the first adapter of FIG. 1.

With continued reference to FIGS. 1 and 2 and specific reference to FIG. 3, the first adapter 24 will be further described. The first adapter 24 is illustrated to include an adapter body 36 which includes a first cavity 38 for receiving the tapered extension 32 of the tray 22, a second cavity 40 for receiving a tapered extension 42 of the stem 20 and a third cavity 44 interconnecting the first cavity 38 and the second cavity 40. The first cavity 38 includes the central axis T and the second cavity 40 includes the central axis S. In the embodiment illustrated, the central axis T and the central axis S are generally parallel to one another and spaced apart. Insofar as the first adapter 24 provides a 5 mm offset, the central axis T and central axis S are spaced apart 5 mm.

With specific reference to FIG. 3, the first cavity 38 includes a first portion 48 for directly receiving the tapered extension 32 of the tray 22. The first portion 48 tapers slightly as it extends into the adapter body 36 from a top end 50 of the adapter body 36. The second cavity 40 similarly includes a second portion 52 for directly receiving the tapered extension 42. The second portion 52 tapers slightly as it extends into the adapter body 36 from a lower end 54 of the adapter body 36. As best seen in FIG. 2, tapered extension 32 and first portion 48 define complementary tapered surfaces that mate in a Morse taper press fit. Similarly, the tapered extension 42 and second portion 52 define complementary tapered surfaces that mate in a Morse taper press fit. As will be appreciated, the circular conical surfaces of tapered extension 32, tapered extension 42, first portion 48 and second portion 52 allow rotation therebetween and enable offset $O_1$ to extend in any direction normal to central axis S and central axis T. The Morse taper press fit connections are impacted in order to lock the complementary surfaces prior to tightening flexible fastener 26.

With particular reference to FIG. 2, stem 20 has a main body portion 60 with a surface 62 defining fins 64 and is illustrated to include an internally threaded aperture 68 within the tapered extension 42. Stem 20 is configured to mount within the intramedullary canal of a tibia. It would be appreciated that, while first adapter 24 is described as having cavities for receiving male tapers, or extensions, first adapter 24 could be provided with coupling portions in the form of extensions and stem 20 and tray 22 provided with complementary coupling portions in the form of cavities. It would also be appreciated that tapered extension 32, tapered extension 42, first portion 48, and second portion 52, while illustrated as defining conical surfaces, could also define surfaces of other shapes, including cylindrical surfaces.

Figure 5:
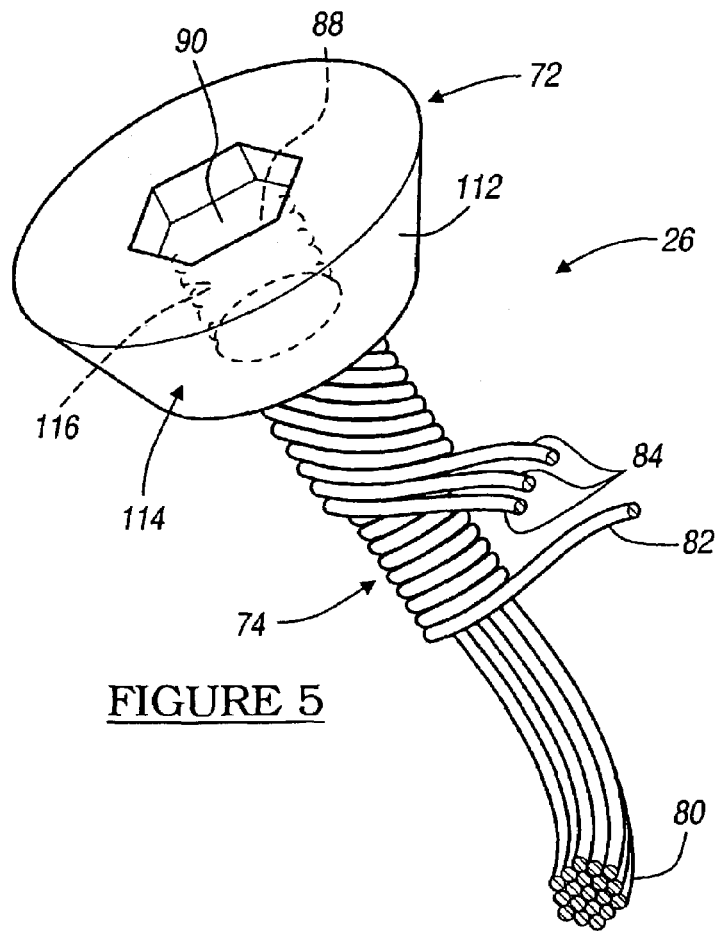
FIG. 5 is a partial exploded sectional view of the fastener of FIG. 1 taken along the line 5—5 of FIG. 4.
Figure 6:
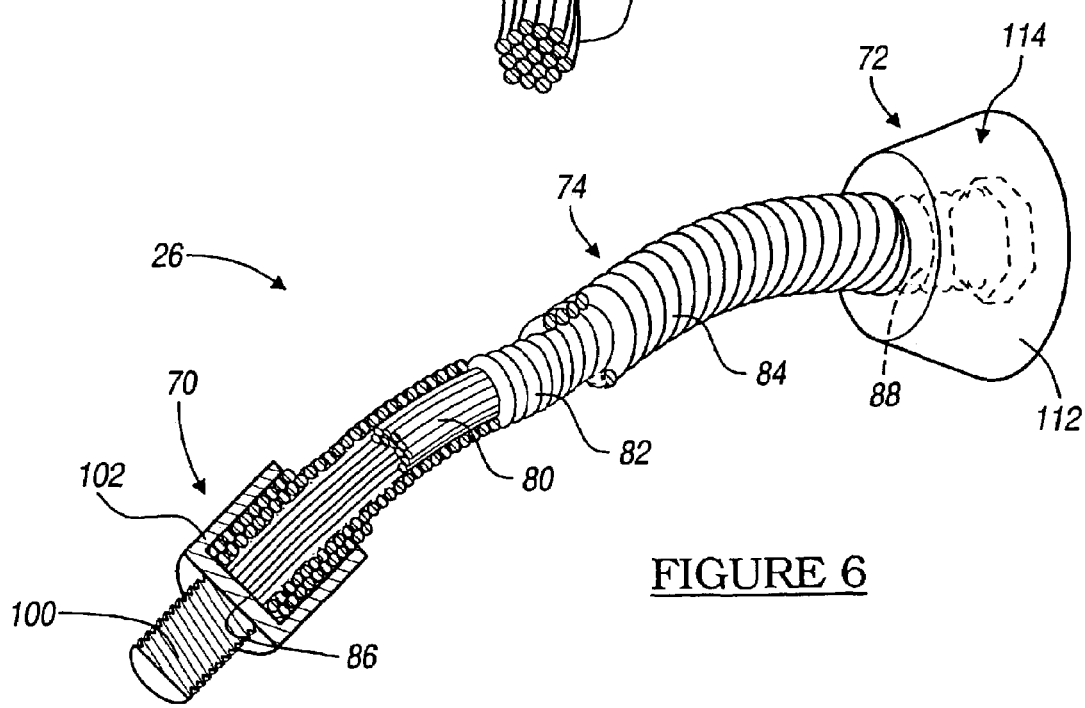
FIG. 6 is a partial sectional view of the fastener of FIG. 5.

With particular reference to FIGS. 5 and 6, flexible fastener 26 is illustrated in greater detail. Flexible fastener 26 includes a first connecting portion 70, a second connecting portion 72 and a flexible shaft 74 coupled therebetween. Flexible shaft 74 includes longitudinal wires, or cables, 80, an inner spiral wire 82, outer spiral wires 84, a first end 86, and a second end 88. Longitudinal wires 80 extend within flexible shaft 74 from the first connecting portion 70, at first end 86, to the second connecting portion 72, at the second end 88. Inner spiral wire 82 is tightly wrapped or spiraled around longitudinal wires 80 from first end 86 to second end 88. Outer spiral wires 84 are preferably three parallel wires that are wrapped or spiraled around inner spiral wire 82 and longitudinal wires 80 from first end 86 to second end 88. A spot weld 90 is located at first end 86 and second end 88. Spot welds 90 join longitudinal wires 80, inner spiral wire 82 and outer spiral wires 84 to prevent unraveling of flexible shaft 74. The first connecting portion 70 is shown to include a threaded portion 100 connected to a sleeve 102. Flexible shaft 74 is interposed within sleeve 102 and sleeve 102 is affixed thereto in order to prevent relative rotation therebetween. The threaded portion 100 is externally threaded for engaging the internally threaded aperture 68 of the tapered extension 42 of the stem 20.

The second connecting portion 72 is illustrated in FIGS. 5 and 6 to be a tapered bolt head. The second connecting portion 72 includes a tapered body 112 defining a frusto-conical surface 114 with an inner cylindrical bore 116 and a tool engaging portion 118. As best seen in FIG. 5, flexible shaft 74 is interposed within cylindrical bore 116 and spot weld 90 is applied thereto. In the embodiment shown, spot weld 90 connects flexible shaft 74 to the second connecting portion 72 while preventing unraveling of flexible shaft 74, as discussed above. The tool engaging portion 118 is adapted to couple with a surgical tool for rotation of flexible fastener 26, as discussed below.

Figure 7:
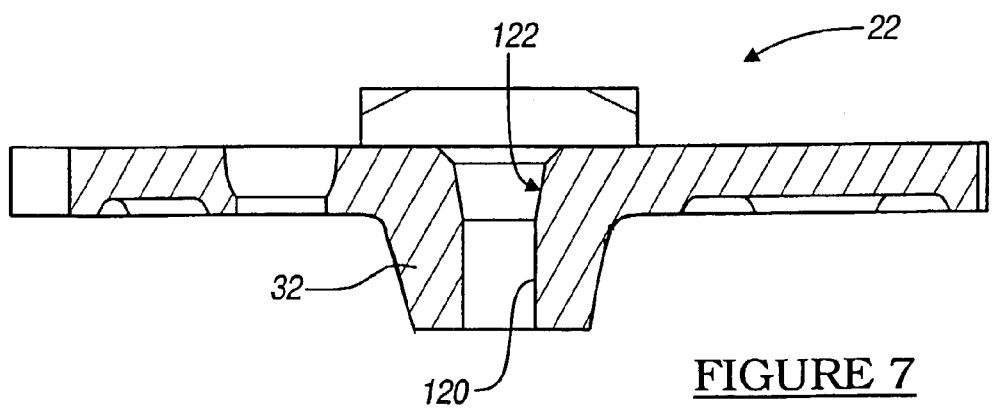
FIG. 7 is a sectional view of a tibial tray according to the teachings of the present invention.

As best seen in FIGS. 2 and 7, tray 22 includes a central aperture 120 with a tapered surface 122 that mates with frusto-conical surface 114 of second connecting portion 72. When assembled, flexible fastener 26 extends through central aperture 120 and the second connecting portion 72 is in contact with tapered surface 122.

Upon selection by the surgeon of the first adapter 24, the adapter body 36 is placed over the tapered extension 42 of the stem 20 such that the tapered extension 42 is received within the second portion 52 of the second cavity 40. The adapter body 36 is rotated about the axis S to provide the offset in the desired direction. The first portion 48 of the first cavity 38 is now superposed on the tapered extension 32 of the tray 22. Tray 22 is rotated relative first adapter 24 until a desired orientation therebetween is provided. The stem 20 is secured to the tray 22 by the flexible fastener 26 which extends through the central aperture 120, the first cavity 38, the second cavity 40 and the third cavity 44, wherein threaded portion 100 threadably engages the internally threaded aperture 68. Rotation of the flexible fastener 26 in a clockwise direction causes the tray 22, first adapter 24, and stem 20 to be drawn together. In this manner, proper alignment of stem 20 and tray 22 can be monitored as tibial component 12 is assembled. Flexible fastener is further rotated with a surgical tool until a preselected amount of torque is achieved. Thus, the first adapter 24 and the flexible fastener 26 provide a rigid connection between tray 22 and stem 20 for a knee joint prosthesis.

Referring now to FIG. 4, second adapter 34 will be further described. The second adapter 34 is illustrated to include an adapter body 36' which includes a first cavity 38' for receiving the tapered extension 32 of the tray 22, a second cavity 40' for receiving a tapered extension 42 of the stem 20 and a third cavity 44' interconnecting the first cavity 38' and the second cavity 40'. The first cavity 38' includes a first central axis T' and the second cavity 40' includes a second central axis S'. In the embodiment illustrated, the first central axis T' and the second central axis S' are parallel to one another and spaced apart providing the second offset $O_2$. Insofar as the second adapter 34 provides a 2 mm offset, the first and second central axes T' and S' are spaced apart 2 mm. The second adapter 34 is assembled in a manner similar to first adapter 24 as described herein. Additional adapters, with varying amounts of preselected offset, can be combined with stem 20, tray 22, first adapter 24, second adapter 34 and flexible fastener 26 to provide a tibial component kit with a minimal amount of inventory.

While flexible shaft 74 is illustrated to include wires, it would be appreciated by one skilled in the art that flexible shaft 74 may comprise other materials that provide the required strength, durability, compatibility, and torsion transmitting capabilities. It would also be appreciated that flexible shaft 74 could comprise any number of longitudinal wires 80 with any number of inner spiral wires 82 coiled thereon and any number of outer spiral wires 84 coiled thereon. It would also be appreciated that while inner spiral wire 82 and outer spiral wires 84 are illustrated in FIGS. 5 and 6 as being wound in the same direction about flexible shaft 74, outer spiral wires 84 and inner spiral wires 82 could be wrapped in opposite directions along the length of longitudinal wires 80 to form flexible shaft 74. In the embodiment shown, outer spiral wires 84 are wrapped in a clockwise direction from second end 88 to first end 86 when threaded portion 100 is right-hand threaded. In this manner, flexible fastener 26 is capable of transmitting torque from second connecting portion 72 to first connecting portion 70 as flexible fastener 26 is tightened into stem 20. It would also be recognized by one skilled in the art that longitudinal wires 80, inner spiral wires 82 and outer spiral wires 84 can be constructed of any material compatible with a prosthesis including preselected stainless steels and titanium.

In use, a surgeon determines the desired offset for a tibial component 12. The femoral component 14 is installed. The surgeon will resect a tibial plateau to provide an appropriate surface for the selected type of knee joint prosthesis 10. The intramedullary canal of the tibia is reamed and prepared for implantation. The tibial component 12 is implanted within the intramedullary canal. The tibial component 12 can be either preassembled with a stem, adapter, tray and fastener for implantation, or the stem can be implanted before the tibial component 12 is fully assembled. As will be appreciated, the knee joint prosthesis 10 can be supplied as a kit including the femoral component 14, bearing 16, and tibial component 12. The kit is provided with adapters of various offsets, for example, offsets of about 0 mm, 2 mm, 4 mm, 6 mm, 8 mm, and 10 mm, inclusively. The kit can also be provided with a selection of stems 20 and trays 22 to accommodate anatomical variations of prosthesis recipients. As will also be appreciated, first adapter 24 may be constructed such that central axis S and central axis T are not parallel, or never intersect.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A modular assembly for a joint prosthesis comprising:
   an implant base having a first coupling portion;
   a stem operable to engage a canal of a bone, the stem having a main body portion and a second coupling portion;
   an adapter body configured to establish a relative offset between the first coupling portion and the second coupling portion; and
   a flexible fastener interconnecting the first coupling portion and the second coupling portion, including:
   a flexible shaft having a first end and a second end;
   a first connecting portion connected to the first end; and
   a second connecting portion connected to the second end;
   wherein the flexible fastener is operable to have the first end on a different axis than the second end.

2. The assembly of claim 1 wherein the second connecting portion comprises a tapered head.

3. The assembly of claim 1 wherein the first connecting portion is threaded to threadably engage with an internally threaded aperture formed within the first coupling portion.

4. The assembly of claim 1 wherein the flexible shaft comprises:
   at least one longitudinal wire extending from the first end to the second end;
   an inner spiral wire wrapped around the longitudinal wire from the first end to the second end; and
   an outer spiral wire wrapped around the inner spiral wire from the first end to the second end.

5. The assembly of claim 1, further comprising a plurality of adapter bodies, wherein each adapter body has a preselected offset.

6. The assembly of claim 5, wherein the preselected offset of each adapter body is within the range of about 0 mm to about 10 mm.

7. The assembly of claim 1, wherein the flexible fastener is interposed within a cavity of the adapter body.

8. The assembly of claim 1, wherein the adapter body defines a first cavity receiving the first coupling portion, a second cavity receiving the second coupling portion, and a central cavity intersecting the first cavity and the second cavity.

9. The assembly of claim 8, wherein the first coupling portion has an outer frusto-conical surface configured to mate with an interior surface of the adapter body, the interior surface defining at least a portion of the first cavity.

10. The assembly of claim 8, wherein the second coupling portion has an outer frusto-conical surface configured to mate with an interior surface of the adapter body, the interior surface defining at least a portion of the second cavity.

11. The assembly of claim 1, wherein the first coupling portion has an inner frusto-conical surface configured to mate with an exterior surface of the adapter body.

12. The assembly of claim 1, wherein the second coupling portion has an inner frusto-conical surface configured to mate with an exterior surface of the adapter body.

13. The assembly of claim 1, further comprising a first component and a second component, wherein the implant base defines at least a portion of the first component.

14. The assembly of claim 13, wherein the first component is a tibial component and the second component is a femoral component.

15. An orthopedic implant operable to be positioned relative to a femur and a tibia in an anatomy, comprising:
   a tibial tray operable to extend from the tibia having a first coupling;
   a stem operable to be positioned in an intramedullary canal of the tibia and having a second coupling;
   an adapter having a third coupling that couples to the first coupling and a fourth coupling that couples to the second coupling, wherein the third coupling defines a first axis and the fourth coupling defines a second axis, the adapter operable to be interposed between the first coupling and the second coupling; and
   a fastener operable to engage at least one of the tibial tray, the stem, the adapter, or combinations thereof extend through the adapter, wherein the fastener extends between a first end and a second end such that the first end is aligned with the first axis and the second end is aligned with the second axis;
   wherein the fastener includes a first engaging portion and a second engaging portion and a flexible shank interconnecting the first engaging portion and the second engaging portion and secures the tibial tray to the stem through the adapter.

16. The implant of claim 15, wherein the first coupling defines a male taper.

17. The implant of claim 16, wherein the second coupling defines a male taper.

18. The implant of claim 15, wherein the adapter defines a male taper.

19. The implant of claim 15, wherein the first axis is offset from the second axis in a range of about 0 mm to about 10 mm.

20. The implant of claim 15, wherein the fastener is interposed through a cavity in the adapter.

21. The implant of claim 15, further comprising a first component that articulates with a second component, wherein the first portion, the second portion, the adapter and the fastener define at least a portion of the first component.

22. The implant of claim 21, wherein the first component is a tibial component and the second component is a femoral component.

23. The orthopedic implant of claim 15, wherein the first axis does not extend along the second axis.

* * * * *